(12) United States Patent
Banville et al.

(10) Patent No.: US 9,198,826 B2
(45) Date of Patent: Dec. 1, 2015

(54) CPR CHEST COMPRESSION MACHINE STOPPING TO DETECT PATIENT RECOVERY

(75) Inventors: Isabelle L. Banville, Newcastle, WA (US); Fred W. Chapman, Renton, WA (US); Joseph L. Sullivan, Kirkland, WA (US); Steven Duke, Edmonds, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 771 days.

(21) Appl. No.: 13/181,384

(22) Filed: Jul. 12, 2011

(65) Prior Publication Data

US 2012/0016279 A1    Jan. 19, 2012

Related U.S. Application Data

(60) Provisional application No. 61/363,996, filed on Jul. 13, 2010, provisional application No. 61/444,091, filed on Feb. 17, 2011, provisional application No. 61/444,888, filed on Feb. 21, 2011, provisional application No. 61/495,176, filed on Jun. 9, 2011.

(51) Int. Cl.
*A61H 31/00* (2006.01)

(52) U.S. Cl.
CPC ............ *A61H 31/004* (2013.01); *A61H 31/006* (2013.01); *A61H 2201/1246* (2013.01); *A61H 2201/5007* (2013.01); *A61H 2201/5097* (2013.01); *A61H 2230/208* (2013.01); *A61H 2230/305* (2013.01)

(58) Field of Classification Search
CPC .............. A61H 31/004; A61H 31/006; A61H 2201/1246; A61H 2201/5097; A61H 2201/5007; A61H 2230/208; A61H 2230/305

USPC ....................................................... 601/41–44
See application file for complete search history.

(56) References Cited

U.S. PATENT DOCUMENTS

| | | | |
|---|---|---|---|
| 4,198,963 A | 4/1980 | Barkalow et al. | |
| 4,397,306 A | 8/1983 | Weisfeldt et al. | |
| 4,424,806 A | 1/1984 | Newman et al. | |
| 4,928,674 A | 5/1990 | Halperin et al. | |
| 5,020,516 A | 6/1991 | Biondi et al. | |
| 5,261,394 A | 11/1993 | Mulligan et al. | |
| 5,490,820 A | 2/1996 | Schock et al. | |
| 5,743,864 A | 4/1998 | Baldwin, II | |
| 5,997,488 A | 12/1999 | Gelfand et al. | |
| 6,676,613 B2 | 1/2004 | Cantrell et al. | |
| 6,926,682 B2* | 8/2005 | Bystrom et al. | 601/41 |
| 7,008,388 B2 | 3/2006 | Sherman et al. | |
| 7,308,304 B2 | 12/2007 | Hampton et al. | |
| 7,311,680 B2 | 12/2007 | Lenhart et al. | |
| 8,343,081 B2 | 1/2013 | Walker | |
| 2004/0039313 A1* | 2/2004 | Sherman et al. | 601/21 |
| 2004/0230140 A1 | 11/2004 | Steen | |
| 2005/0165335 A1 | 7/2005 | Sherman et al. | |
| 2006/0089574 A1 | 4/2006 | Paradis | |
| 2007/0004992 A1 | 1/2007 | Van Brunt et al. | |
| 2007/0270724 A1 | 11/2007 | Havardsholm et al. | |
| 2008/0103538 A1 | 5/2008 | Walker et al. | |
| 2008/0215102 A1 | 9/2008 | Myklebust et al. | |
| 2008/0312565 A1 | 12/2008 | Celik-Butler et al. | |
| 2010/0022886 A1 | 1/2010 | Ayati et al. | |
| 2010/0222718 A1* | 9/2010 | Freeman et al. | 601/41 |

\* cited by examiner

*Primary Examiner* — Quang D Thanh
(74) *Attorney, Agent, or Firm* — Marger Johnson

(57) ABSTRACT

Embodiments of the present concept are directed to CPR chest compression machines that include a sensor to detect a parameter about a patient, such as an indication of patient recovery, and include a processor that determines whether to cease series of successive compressions on the patient in response to the detected parameter.

33 Claims, 12 Drawing Sheets

*CPR CHEST COMPRESSION MACHINE HAVING STATIC SENSOR*

COMPRESSION STRUCTURE OF CPR
CHEST COMPRESSION MACHINE

SAMPLE COMPRESSION STRUCTURE OF
CPR CHEST COMPRESSION MACHINE

EXAMPLE CPR CHEST COMPRESSION MACHINE

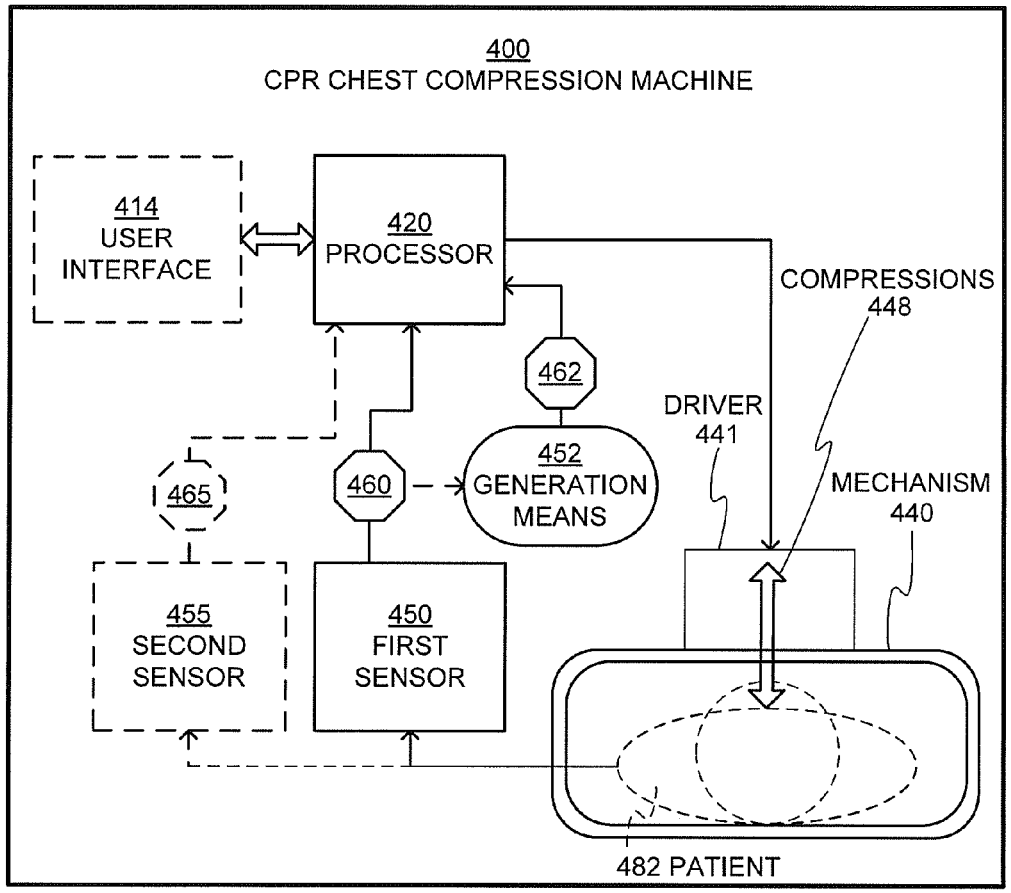
FIG. 4   CPR CHEST COMPRESSION MACHINE HAVING STATIC SENSOR

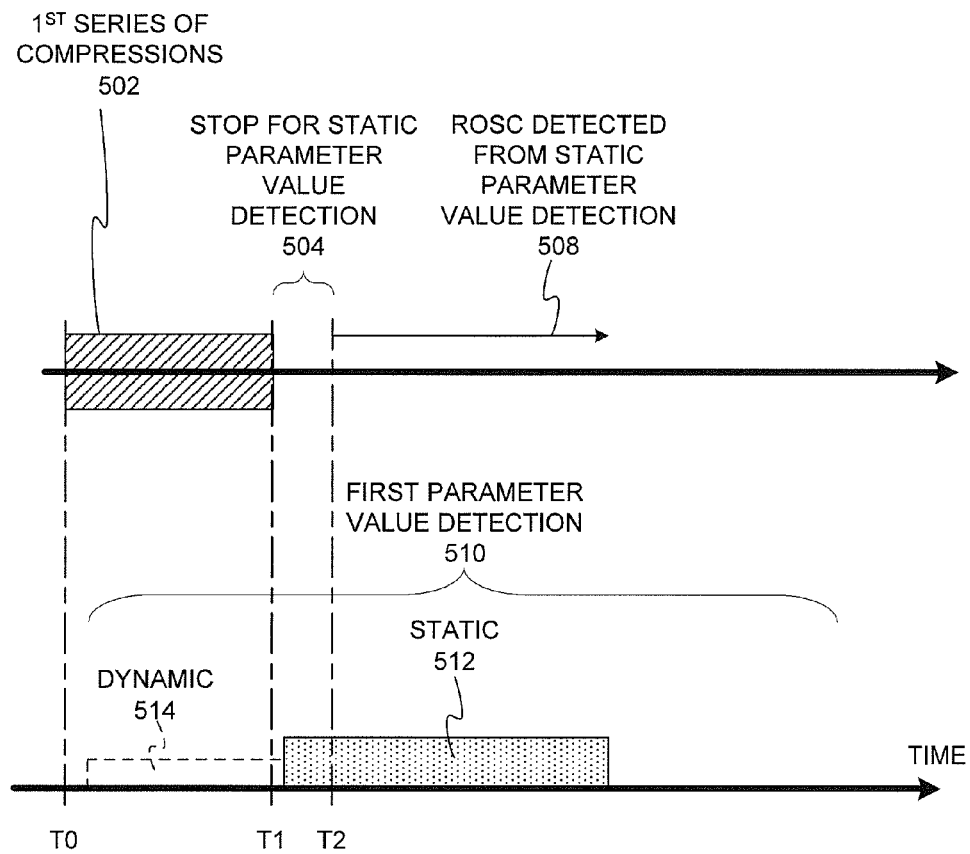
FIG. 5A *TIME LINE OF EXAMPLE STATIC DETECTION PAUSE DURING SUCCESSIVE CPR CHEST COMPRESSIONS*

TIME LINE OF EXAMPLE STATIC DETECTION PAUSE DURING SUCCESSIVE CPR CHEST COMPRESSIONS

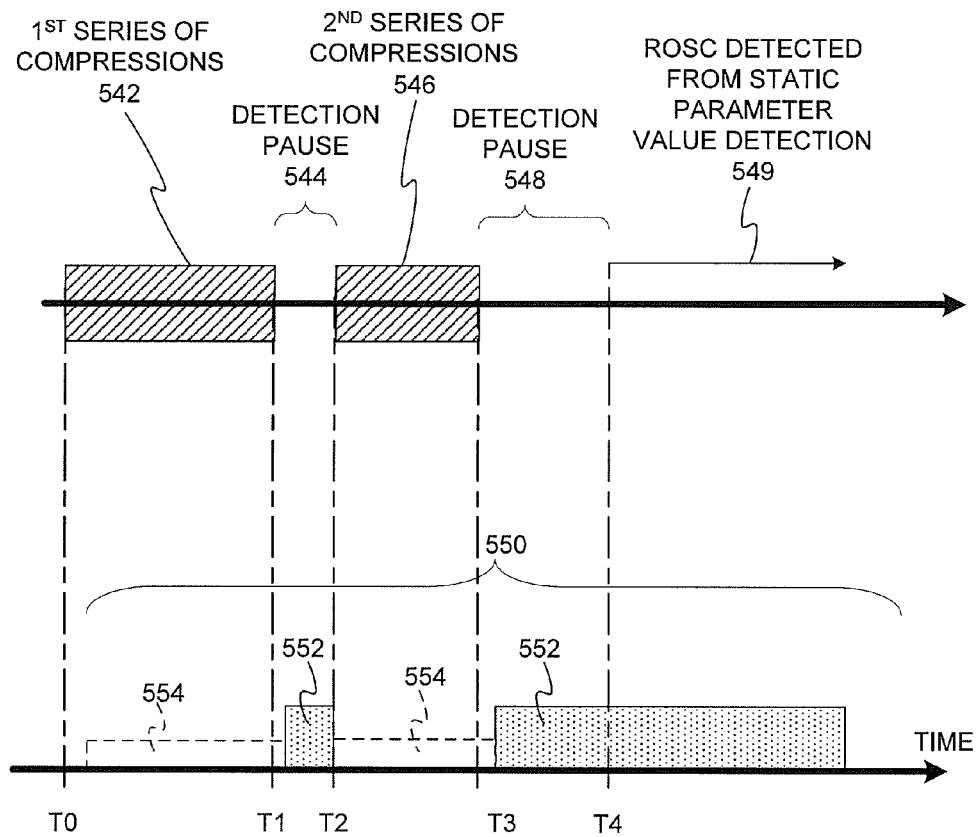
FIG. 5C *TIME LINE OF EXAMPLE STATIC DETECTION PAUSES DURING SUCCESSIVE CPR CHEST COMPRESSIONS*

TIME LINE OF EXAMPLE STATIC DETECTION PAUSES DURING SUCCESSIVE CPR CHEST COMPRESSIONS

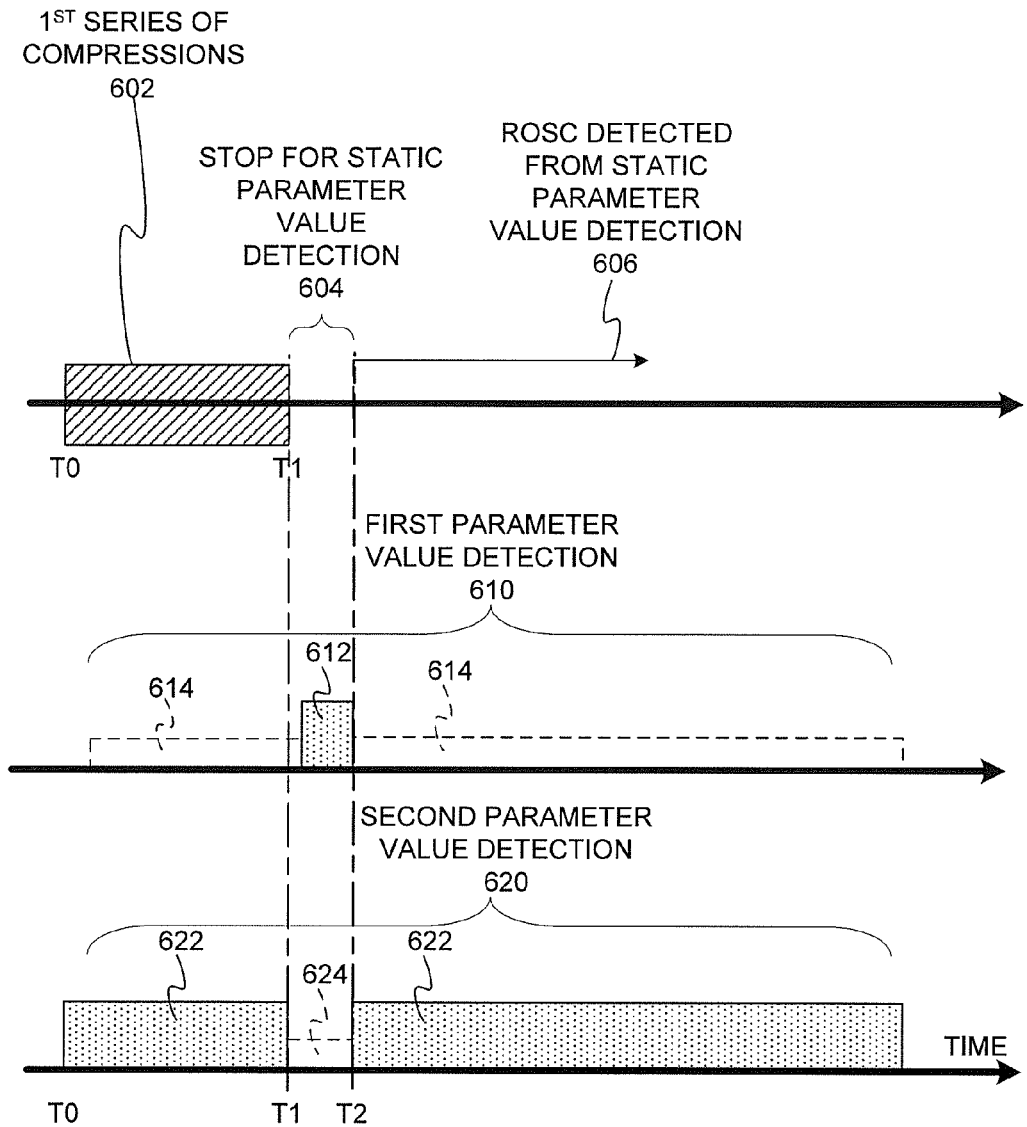
FIG. 6A — *TIME LINE OF EXAMPLE STATIC AND DYNAMIC DETECTION PROCESSES DURING SUCCESSIVE CPR CHEST COMPRESSIONS*

*TIME LINE OF EXAMPLE STATIC AND DYNAMIC DETECTION PROCESSES DURING SUCCESSIVE CPR CHEST COMPRESSIONS*

TIME LINE OF EXAMPLE STATIC AND DYNAMIC DETECTION PROCESSES DURING SUCCESSIVE CPR CHEST COMPRESSIONS

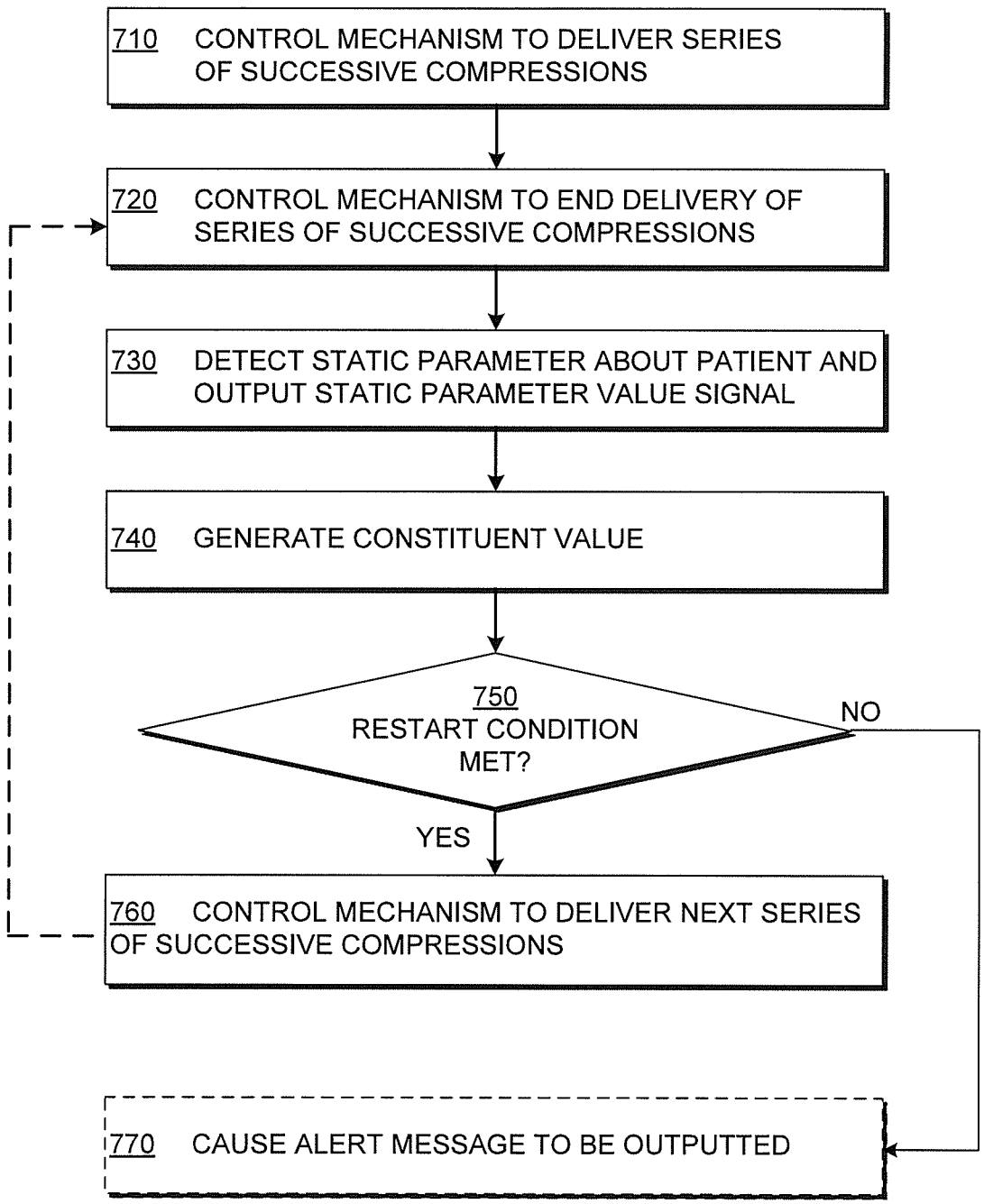
FIG. 7 *METHOD FOR OPERATING CPR CHEST COMPRESSION MACHINE*

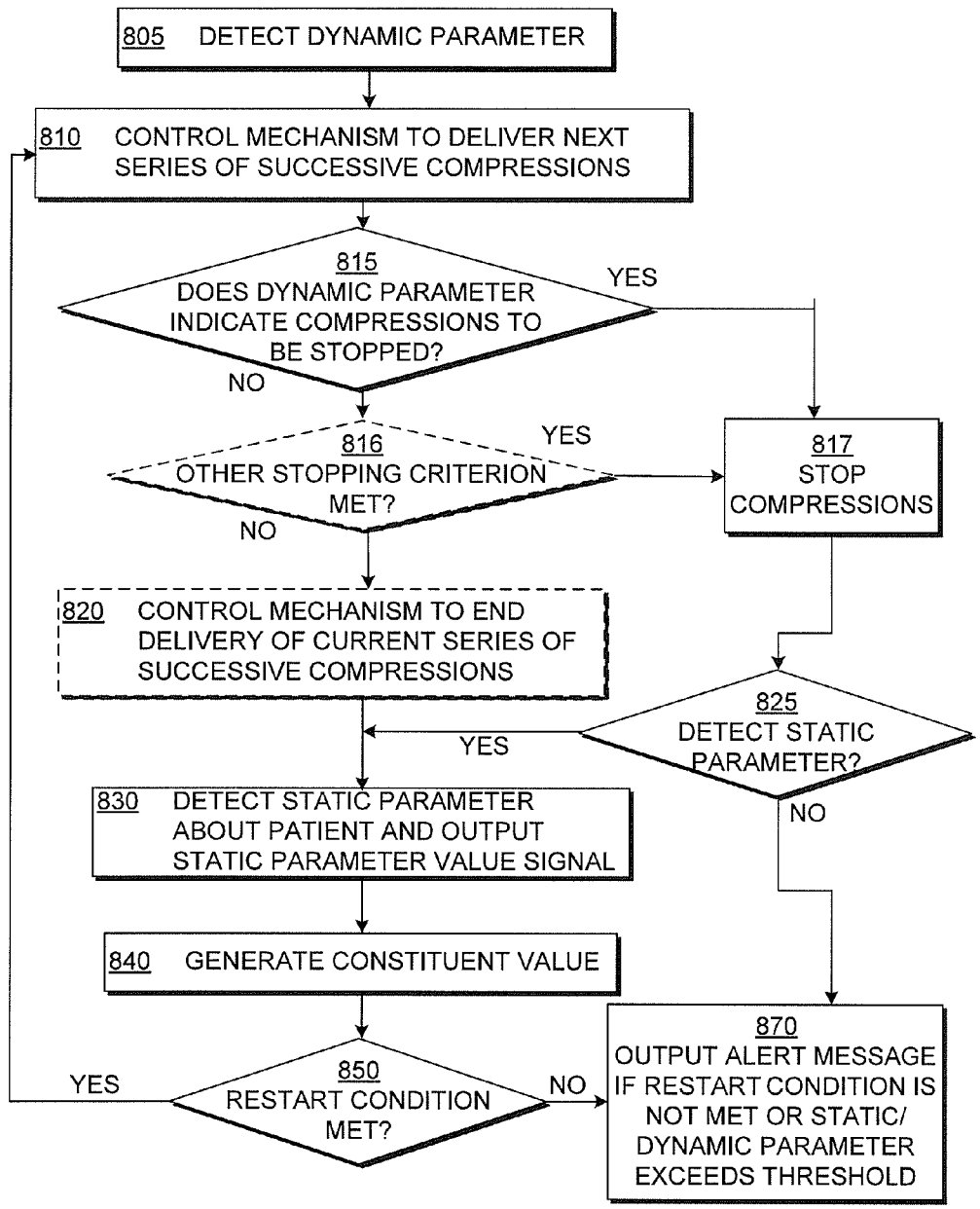
FIG. 8  *METHOD FOR OPERATING CPR CHEST COMPRESSION MACHINE*

CPR CHEST COMPRESSION MACHINE STOPPING TO DETECT PATIENT RECOVERY

CROSS REFERENCE TO RELATED PATENT APPLICATIONS

This patent application claims priority from the following Provisional Patent Applications: U.S. Provisional Patent Application Ser. No. 61/363,996, filed on Jul. 13, 2010; U.S. Provisional Patent Application Ser. No. 61/444,091, filed on Feb. 17, 2011; U.S. Provisional Patent Application Ser. No. 61/444,888, filed on Feb. 21, 2011; U.S. Provisional Patent Application Ser. No. 61/495,176, filed on Jun. 9, 2011. The disclosure of each provisional is hereby incorporated by reference for all purposes.

FIELD

This invention generally relates to CPR chest compression machines.

BACKGROUND

In certain types of medical emergencies, Cardio-Pulmonary Resuscitation ("CPR") needs to be delivered to a patient. CPR includes repeatedly compressing the chest of the patient, to cause their blood to circulate some. CPR also includes delivering rescue breaths to the patient. A number of people are trained in CPR, just in case, even though they are not trained in the medical professions.

The chest compressions are intended to prevent damage to organs like the brain. In some instances, the chest compressions merely maintain the patient, until a more definite therapy is made available, such as defibrillation. Defibrillation is an electrical shock deliberately delivered to a person, in the hope of correcting their heart rhythm.

A problem is that CPR is sometimes ineffective for preventing damage to the patient. That can happen whether or not the rescuer who performs the CPR is part of the medical profession. The most frequent example of such ineffectiveness is compressions that are not deep enough, or not frequent enough. Even the best trained rescuers can become fatigued after delivering CPR, with the compressions deteriorating in quality. And that is without even accounting for the emotions of the moment, which might impact a lay rescuer.

The risk of ineffective chest compressions has been addressed in part by defibrillator manufacturers. Some defibrillators nowadays issue verbal and visual prompts and other instructions as to how CPR is to be performed. These are often according to the guidelines of medical experts, such as the American Heart Association. These prompts and other instructions can help the rescuer focus better, even if the latter cannot remember their training.

The risk of ineffective chest compressions has been additionally addressed with CPR feedback devices. These devices actually detect the depth and frequency of compressions that the rescuer is performing, and give feedback that is specifically attuned to what the rescuer is doing. This feedback can be in accordance with the how well the rescuer is meeting the above mentioned guidelines, especially in achieving the indicated depth of compressions.

Reaching the appropriate depth is difficult. The recommended depth is a range. If the actual depth is less than the range, not enough blood is moved within the patient. If the depth exceeds the range, the patient's ribs may break. And, even for experienced rescuers, it is sometimes hard to discern the appropriate depth. Reaching the appropriate depth is even more difficult if the patient is on a flexible mattress that partly recedes, as the rescuer is pushing from the top. And CPR compressions are even more challenging, if the rescuer has to deliver them in a moving ambulance.

The risk of ineffective chest compressions has been moreover addressed with CPR chest compression machines. Such machines have been known by a number of names, such as mechanical CPR devices, cardiac compressors, external chest compression machines, and so on.

CPR chest compression machines repeatedly compress and release the chest of the patient. Such machines can be programmed so that they will compress and release at the recommended rate, and always reach a specific depth within the recommended range.

Although CPR chest compression machines can be used in conjunction with external defibrillators, not all ailments for which a CPR chest compression machine is used require defibrillation. Hence, many treatment protocols instruct the use of CPR without the need to electrically shock the patient's heart.

Although it is generally good to perform CPR chest compressions, it is sometimes difficult to know when to stop compressions. A CPR machine, or even a rescuer may not notice that a patient has regained spontaneous circulation and compressions may continue to be given even though the patient's heart is beating. Occasionally the patient may regain consciousness during compressions. This may cause the patient pain and discomfort, as well as potentially scaring them and causing additional emotional or physical trauma.

Even when the CPR chest compression machine helps the patient return to spontaneous circulation while they are still comatose, it is still desirable to stop the CPR chest compression machine promptly because 1) its compressions can interfere with the normal filling of heart chambers between spontaneous heart contractions, thus decreasing the cardiac output caused by those spontaneous heart contractions, and 2) its compressions can, under certain circumstances, increase the probability that the heart will return to ventricular fibrillation.

BRIEF SUMMARY

The present description gives instances of medical devices, systems, and methods, the use of which may help overcome problems and limitations of the prior art.

In particular, embodiments of the present concept are directed to CPR chest compression machines that include a sensor to detect a parameter about a patient, such as an indication of patient recovery, and include a processor that determines whether to cease series of successive compressions on the patient in response to the detected parameter.

In some embodiments, a machine for performing Cardio-Pulmonary Resuscitation ("CPR") chest compressions includes a mechanism for delivering successive compressions to a chest of a patient, a driver for driving the mechanism, and a processor for controlling the driver to drive the mechanism to deliver successive chest compressions or stop the delivery of successive chest compressions. In these embodiments, the CPR chest compression machine also includes a sensor adapted to detect a parameter about the patient and output a sensor signal indicative of a value of the parameter, and includes a generation means for automatically generating a constituent value. Here, the processor is configured to stop delivery of a series of successive compressions for a static value of the parameter to be detected by the sensor, to determine from the constituent value whether a restart condition is met, and to implement another series of successive chest compressions if the restart condition is met.

In other embodiments, a method for a Cardio-Pulmonary Resuscitation ("CPR") compression machine having a mechanism for delivering successive compressions to a chest of a patient is disclosed. This method includes controlling the mechanism to deliver and end delivery of a first series of successive compressions to the chest of the patient, and detecting a static value of a first parameter about the patient while the patient is not receiving chest compressions. A first sensor signal indicative of the static value is outputted, and a constituent value is automatically generated. It is then determined from the constituent value whether a restart condition has been met. If the restart condition is met, the mechanism is controlled to deliver a second series of successive compressions.

An advantage over the prior art is that patient recovery can be detected during automatic series of successive chest compressions and the compressions can be paused or ended so that the patient is not put at risk for feeling pain or discomfort from the chest compressions.

These and other features and advantages of this description will become more readily apparent from the following Detailed Description, which proceeds with reference to the drawings, in which:

BRIEF DESCRIPTION OF THE DRAWINGS

FIG. 4 is a diagram of a CPR chest compression machine according to embodiments.

FIGS. 5A, 5B, 5C, and 5D are timeline diagrams illustrating sample detection pauses for detecting parameters about a patient during successive chest compressions according to embodiments.

FIGS. 6A, 6B, and 6C are timeline diagrams illustrating dynamic sample detection periods for detecting parameters about a patient during successive chest compressions according to embodiments.

FIG. 7 is a flowchart for illustrating methods according to embodiments.

FIG. 8 is another flowchart for illustrating methods according to embodiments.

DETAILED DESCRIPTION

As has been mentioned, the present description is about medical devices, systems, and methods for stopping a CPR chest compression machine to detect patient recovery.

Embodiments are now described in more detail.

Figure 1:
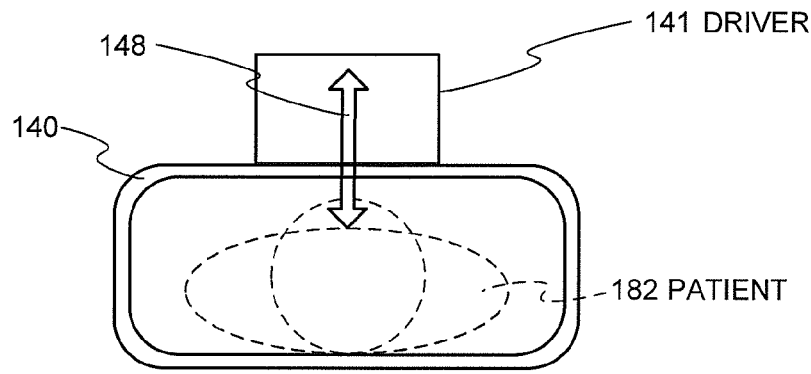
FIG. 1 is a diagram of an abstracted compression structure of a CPR chest compression machine in the prior art.

FIG. 1 is a diagram of an abstracted compression structure 140 of a CPR chest compression machine in the prior art. A patient 182 is placed within compression structure 140. A driver 141 is then controlled to drive the compression structure 140 to repeatedly compresses and releases their chest. These compressions and releases are designated by arrow 148, regardless of how effectuated.

Compression structure 140 is shown as reaching around the chest of patient 182. This alleviates the above-mentioned problem of the patient being on a flexible mattress, which causes ineffective CPR. Indeed, compressions 148 are with respect to compression structure 140, not the mattress. But structure 140 typically does not cover, for example, the head of patient 182.

Compression structure 140 is abstracted, in that it may be implemented in any number of ways. In some embodiments, a belt squeezes and releases the patient's chest. A piston embodiment is now described.

Figure 2:
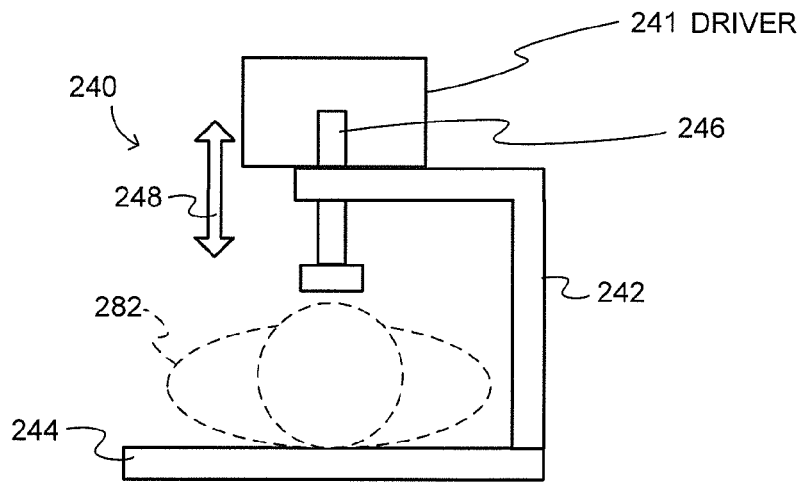
FIG. 2 is a diagram of a sample compression structure of a CPR chest compression machine in the prior art.

FIG. 2 is a diagram of a sample compression structure 240 of a CPR chest compression machine in the prior art. Structure 240 includes a member 242. A backboard 242 is attached to member 242. Patient 282 is placed on backboard 244. A piston 246 is attached to member 242. A driver 241 is controlled to drive the piston 246 automatically up and down to deliver compressions and releases 248.

Figure 3:
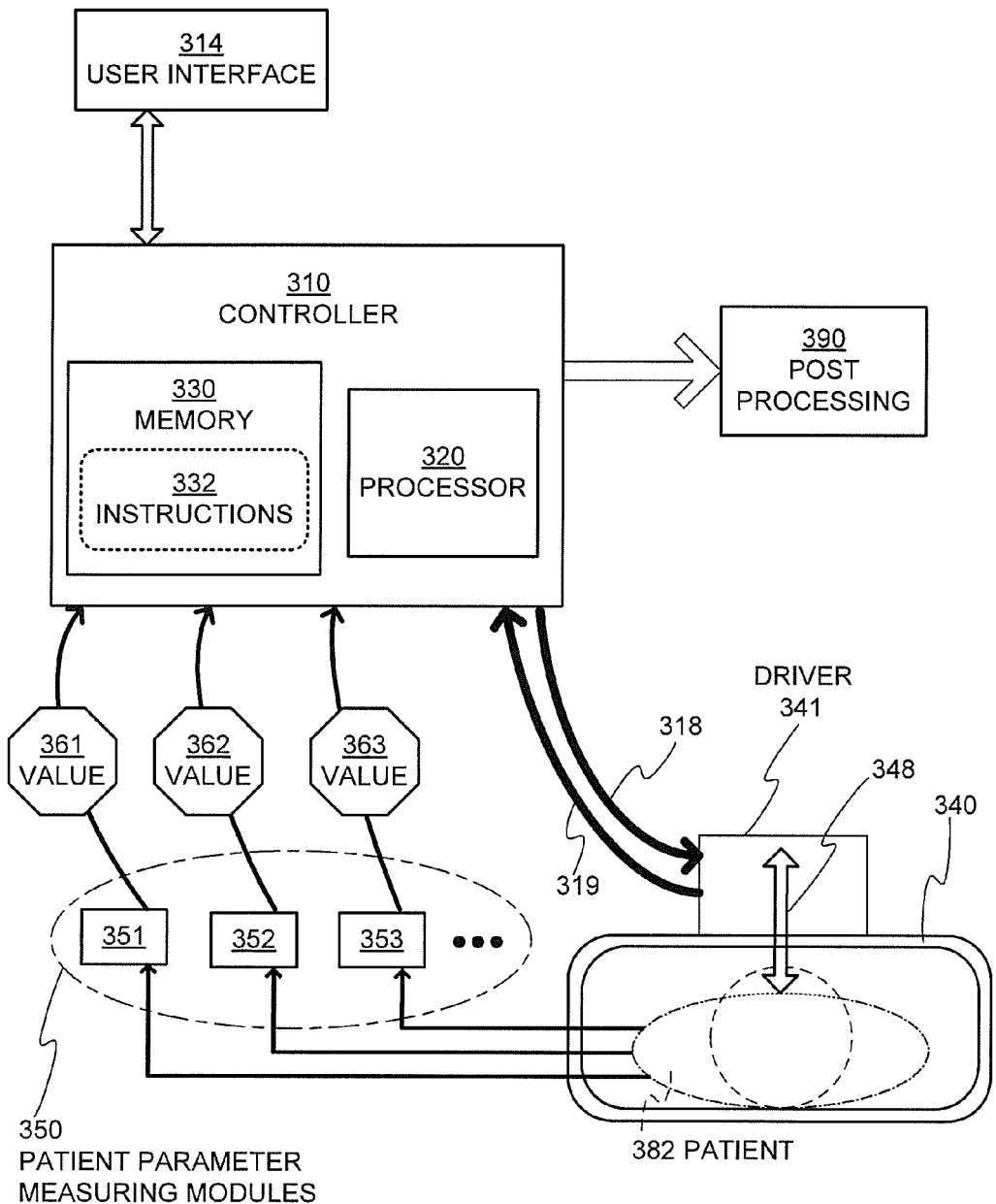
FIG. 3 is a diagram of a controller for a compression structure of a CPR chest compression machine according to embodiments.

FIG. 3 is a diagram of a controller 310 according to embodiments. Controller 310 may be coupled with a User Interface 314, for receiving user instructions, and for outputting data.

Controller 310 includes a processor 320. Processor 320 can be implemented in any number of ways, such as with a microprocessor, Application Specific Integration Circuits, programmable logic circuits, general processors, etc. While a specific use is described for processor 320, it will be understood that processor 320 can either be standalone for this specific use, or also perform other acts.

Controller 310 additionally includes a memory 330 coupled with processor 320. Memory 330 can be implemented by one or more memory chips. Memory 330 stores instructions 332 for execution by processor 320. While a specific use is described for memory 330, it will be understood that memory 330 can hold additional data.

Controller 310 is intended to control a driver 341 which drives, according to arrow 318, compressions 348 of a compression structure 340 of a CPR chest compression machine. Compressions 348 are delivered to a patient 382, who is in the compression structure 340. In addition, controller 310 receives data about compression structure 340, for example a time profile of compressions, according to arrow 319.

Controller 310 may be implemented together with the driver 341 and compression structure 340, in a single CPR chest compression machine. In such embodiments, arrow 318 is internal to such a CPR chest compression machine. Alternately, controller 310 may be hosted by a different machine, which communicates with the driver 341 of a CPR chest compression machine that uses compression structure 340. Such communication can be wired or wireless. The different machine can be any kind of device, such as a medical device. One such example is described in commonly assigned U.S. Pat. No. 7,308,304, titled "COOPERATING DEFIBRILLATORS AND EXTERNAL CHEST COMPRESSION MACHINES", the disclosure of which is incorporated by reference. Similarly, User Interface 314 may be implemented on the CPR chest compression machine, or on a host device.

In some embodiments, a group 350 of patient parameter measuring modules is also provided. Group 350 is shown as including modules 351, 352, 353, . . . , for measuring parameters of patient 382. These parameters can include Arterial Systolic Blood Pressure (ABSP), blood oxygen saturation (SpO2), ventilation measured as End-Tidal CO2 (ETCO2), temperature, detection of pulse, etc. In addition, these parameters can include what is detected by defibrillator electrodes that may be attached to patient 382, such as ECG and impedance. Modules 351, 352, 353, . . . can be implemented either on a separate standalone monitor device, or on the same CPR chest compression machine as compression structure 340.

Modules 351, 352, 353, . . . can be implemented either on the same device as controller 310 or not, and so on. Many permutations are possible.

Upon sensing patient 382, modules 351, 352, 353 output values 361, 362, 363 respectively, of the parameters they measure. Values 361, 362, 363 are received by controller 310.

Controller 310 further optionally aggregates resuscitation data, for transmission to a post processing module 390. There are a number of possibilities for the resuscitation data, such as event data, time data, patient data, CPR delivery date, and so on. The resuscitation data can include what is learned via arrow 319, values 361, 362, 363, etc. Transmission can be performed in many ways, as will be known to a person skilled in the art. In addition, controller 310 can transmit status data of the CPR chest compression machine that includes compression structure 340.

FIG. 4 is a diagram of another CPR chest compression machine 400 according to embodiments. The CPR chest compression machine 400 includes a mechanism 440 for delivering successive compressions 448 to a chest of a patient 482 and a driver 441 for driving the mechanism. A first sensor 450 in the CPR chest compression machine 400 is adapted to detect a first parameter about the patient 482 and output a first sensor signal indicative of a value 460 of the first parameter. It will be appreciated that value 460 can be called a dynamic value if the first parameter is detected while compressions are being delivered to the chest, and a static value if the first parameter is detected while compressions are not being delivered. Correspondingly, detection during compressions can be called dynamic detection, while detection during a pause can be called static detection.

In addition, a generation means 452 is also included, and is configured to automatically generate a constituent value 462. As will be appreciated by the remainder of this document, any number of elements can be considered to be the generation means, with the corresponding output being the constituent value 462. The final choice of the generation means will depend on the desired embodiment.

The CPR chest compression machine 400 also includes a processor 420 that is operable for controlling the driver 441 to drive the mechanism 440 to deliver the successive compressions 448. Specifically, the processor 420 controls the driver 441 to drive the mechanism 440 to deliver a first series of successive compressions 448, then controls the driver to drive the mechanism to stop delivering the first series of successive compressions for a static value 460 of the first parameter to be detected by the first sensor 450 while the patient 482 is not receiving chest compressions. The processor 420 determines from the constituent value 462 whether a restart condition is met, and then controls the driver 441 to drive the mechanism 440 to start delivering a second series of successive compressions 448 if the restart condition is met. The processor does not control the driver 441 to drive the mechanism 440 to deliver additional successive compressions 448 when the restart condition is not met.

The mechanism 440 that delivers the successive compressions 448 may be implemented in any number of ways, as was described for FIG. 1, for delivering CPR chest compressions to a patient 482 according to CPR protocols to a patient 482.

The restart condition can be dependent on various conditions or measurements in different embodiments, which further define what is also the corresponding generation means. In some embodiments, the generation means 452 is one of a clock or a counter where the constituent value 462 is time. Here, the restart condition is met when a first time interval has elapsed after the first series of successive compressions has stopped. In some embodiments, the restart condition is met also when a data measurement corresponding to the static value 460 has been completed, in addition to what is determined from the constituent value.

In yet other embodiments, the generation means 452 is coupled to receive the first sensor signal from the first sensor 450. Here, the constituent value 462 is a digital rendering of the static value 460 that has been decoded from the first sensor signal. The restart condition may be met when the constituent value 462 is first generated. Alternatively, the restart condition may be met when a computation from the constituent value 462 is indicated as having been completed.

In another example embodiment, the restart condition is met if a determination has been made automatically from the static value that continuing compressions is merited. The first sensor 450 may be further adapted to determine a dynamic value 460 of the first parameter while the patient is receiving chest compressions. Here, the determination of whether the restart condition is met may be based on a comparison of the static value and the dynamic value.

The length of the second or other series of successive compressions may be dependent on the values 460 from the detected first parameter. Similarly, the length of time for the detection of the static value may be variable based on previous measurements. For example, if a first measurement of the static value 460 of the first parameter indicates that a patient is getting closer to recovery, the length of time for the next series of compressions may be shortened and a different constituent value may be used to detect patient recovery during a longer pause in the compressions.

The first series of successive compressions 448 may include ventilation pauses for the patient 482 to receive the ventilations. The patient 482 may receive ventilation from a ventilation machine coupled to the CPR compression machine 400, or from a human provider. In these embodiments, the first series of compressions 448 may be stopped at the beginning of one of the ventilation pauses.

The CPR chest compression machine 400 may also include a user interface 414 in some embodiments. The user interface 414 may be adapted to output an alert message to a user if the restart condition is not met. In other embodiments, the processor 420 causes an alert message to be communicated to a device other than the machine 400 if the restart condition is not met.

The processor 420 may be further adapted to determine whether a stopping criterion is met. Here, the stopping criterion may be determined from the static value 460. When the stopping criterion is met, the processor 420 controls the driver 441 to drive the mechanism 440 to stop delivery of the second series of successive compressions 448 for the first parameter to be detected again by the first sensor 450 while the patient 482 is not receiving chest compressions. The processor 420 may then control the driver 441 to drive the mechanism 440 to start delivering a third series of successive compressions 448 when it is merited.

Alternatively, the second series of successive compressions 448 may be stopped at a second time determined from the static value 460. This determination may be dependent on whether the detected static value 460 exceeds a threshold. The first parameter detected about the patient 482 by the first sensor 450, from which the static value is based, may include many different types of data, such as one or more of the following example parameters: 1) Arterial systolic blood pressure, where the threshold may be, for example, about 80 millimeters of mercury; 2) Blood oxygen saturation, where the threshold may be, for example, about 90 percent; 3) End tidal carbon dioxide, where the threshold may be, for example, about 30 millimeters of mercury; 4) Blood velocity, where the threshold may be, for example, zero ml/s; and/or 5) A patient's ECG, where the threshold may be an ECG threshold criterion that is met. The ECG threshold criterion can be implemented in a number of ways. One example is a QRS rate of above about 60 beats/min. Another example is a QRS acceleration rate of 2 beats/minute every second. Another example may be about an aspect of the morphology of measured QRS complexes. Examples of possible morphologies include a QRS width of less than about 120 msec.

In embodiments where the CPR chest compression machine 400 includes a user interface 414, the user interface may be adapted to output an alert message to a user when the first parameter exceeds the threshold.

FIGS. 5A, 5B, 5C, and 5D are timeline diagrams illustrating sample detection pauses for detecting parameters about a patient during successive chest compressions according to embodiments.

Referring to FIG. 5A, a first series of compressions 502 are initiated at time T0. Detection of the first parameter 510 during this first series of compressions 502 results in dynamic values. At T1, the processor controls the driver to stop the mechanism from delivering the first series of chest compressions 504 so that a static value 512 of the first parameter 510 can be detected. As discussed above, the delivery of successive chest compressions can interfere with some parameter measurements due to the manipulation of the patient's chest. By stopping or pausing the first series of successive chest compressions more precise values about the first parameter may be detected that can be associated with patient recovery. Values thus obtained are called static values. In this illustrated example, the static value 512 based on the measured first parameter indicates that the patient is experiencing a Return Of Spontaneous Circulation (ROSC) 508. Hence, a restart condition is not met since the patient may be recovering consciousness, and additional series of successive compressions are not delivered. However, the first parameter 510 continues to be monitored in case the patient loses ROSC and required additional chest compressions.

Figure 5B:
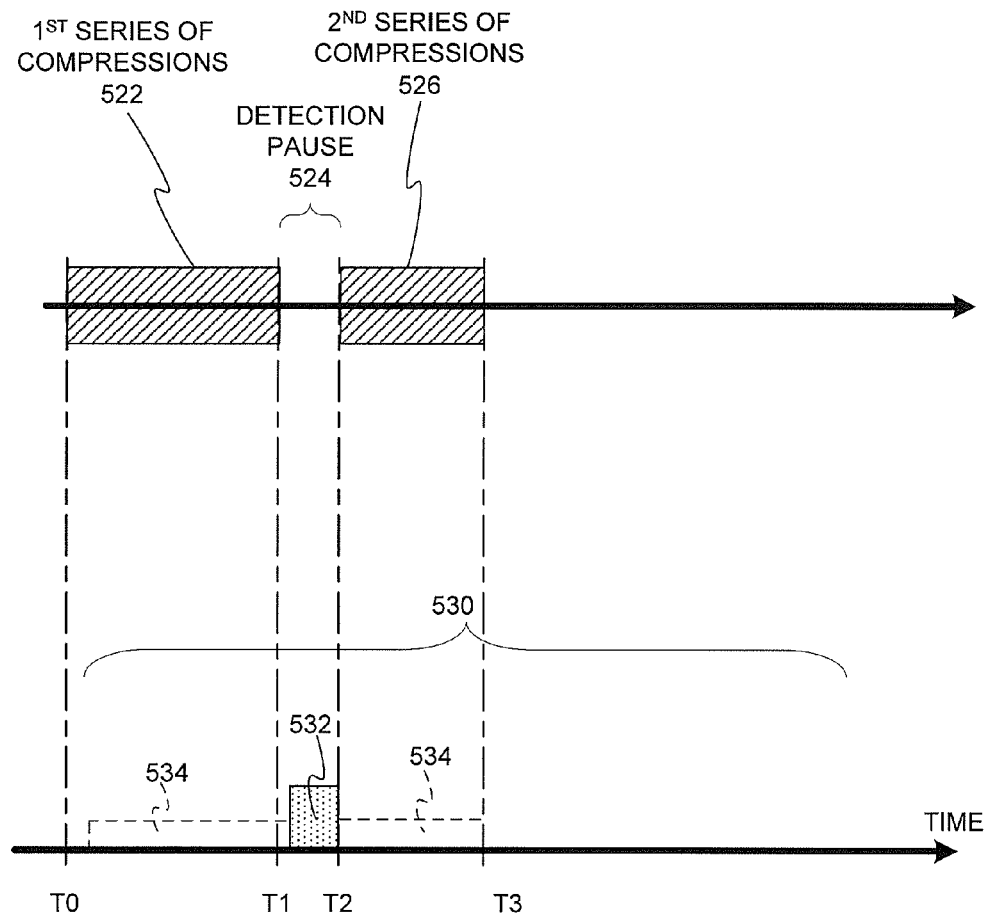

Referring to FIG. 5B, a first series of chest compressions 522 is again initiated at time T0 and a first parameter is detected about the patient 530. The first parameter includes dynamic values 534 during the first series of compressions 522, but returns a static value 532 when the first series of compressions is paused 524 at time T1 for the static measurement of the first parameter. Here, the processor determines from a constituent value that a restart condition was met, and a second series of chest compressions 526 is initiated at time T2. This may be because the static value of the detected first parameter does not meet a predefined threshold. During this second series of chest compressions 526, the detection of the first parameter returns to dynamic values 534.

Referring to FIG. 5C, a first series of chest compressions 542 is again initiated at time T0 and a first parameter 550 is detected about the patient. The first parameter includes dynamic values 554 during the first series of compressions 542, but returns a static value 552 when the first series of compressions is paused 544 at time T1 for the static measurement of the first parameter. Here, the processor determines from a constituent value that a restart condition was met, and a second series of chest compressions 546 is initiated at time T2. During this second series of chest compressions 546, the detection of the first parameter returns to dynamic values 554. Here, however, the second series of chest compressions 546 does not last as long as the first series of chest compressions 542. This may be because the dynamic values 554 of the first parameter indicate that the patient may be recovering and a static measurement is requested to confirm recovery, or because the measured static value 552 detected during the first detection pause 544 may have indicated that the patient was getting close to recovery.

In either case, a second detection pause 548 is initiated at time T3 and a static value 552 of the first parameter 550 is again measured. Here, the generation means may output a different constituent value since the patient may be getting close to recovery and additional detection time for the static value may be required. This results in the second detection 448 pause being longer than the first detection pause 544. In this instance, it is detected that the patient is showing signs of recovery, such as a return of spontaneous circulation 549, from the detected static value and additional chest compressions are not delivered.

Figure 5D:
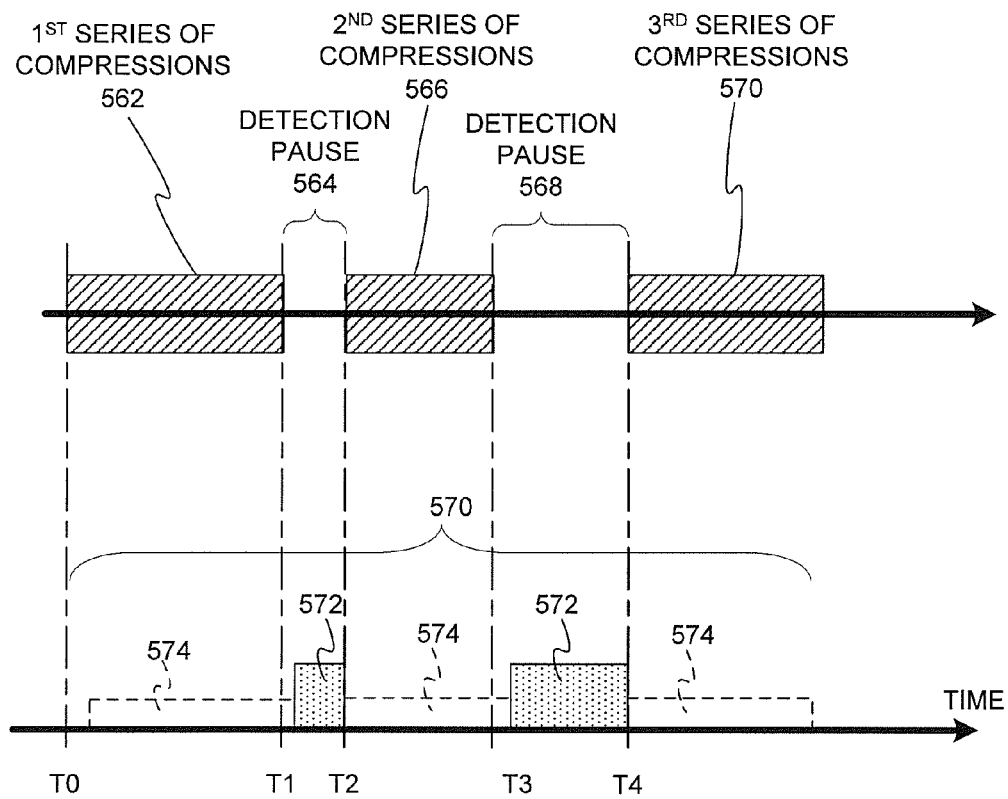

Referring to FIG. 5D, a first series of compressions 562, first detection pause 564, and second series of compressions 568 may be similar to those illustrated in FIG. 5C. Likewise, the detection of the first parameter 570 may again include portions of dynamic value measurement 574 during the compressions, and static value measurement 572 during the detection pauses. In this instance, however, the static value measured from the detected first parameter 570 during the second detection pause 568 does not indicate that the patient has recovered. This may be because the static value of the detected first parameter does not meet a predefined threshold. Hence, a restart condition is met and a third series of compressions 570 is initiated at time T4.

With reference back to FIG. 4, in some embodiments, the CPR chest compression machine 400 includes a second sensor 455 adapted to detect a dynamic value 465 of a second parameter different from the first parameter, the dynamic value detected about the patient 482 while the patient is receiving the first series of chest compressions 448. Here, the first series of chest compressions 448 may be stopped at a first time determined from the dynamic value 465. The dynamic value 465 may be received automatically from the second sensor 455 or may be entered via the user interface 414 by a human rescuer.

Again, the second series of successive compressions 448 may be stopped at a second time determined from the dynamic value 465. This determination may be dependent on whether the detected dynamic value 465 exceeds a threshold.

Similar to the first parameter detected about the patient 482, the second parameter detected from the second sensor 455, from which the dynamic value 465 is detected, may include many different types of data, such as one or more of the following example parameters: 1) Arterial systolic blood pressure, where the threshold may be, for example, about 80 millimeters of mercury; 2) Blood oxygen saturation, where the threshold may be, for example, about 90 percent; 3) End tidal carbon dioxide, where the threshold may be, for example, about 30 millimeters of mercury; 4) Blood velocity, where the threshold may be, for example, zero ml/s; and/or 5) A patient's ECG, where the threshold may be an ECG threshold criterion that is met. Examples of ECG threshold criteria are given above.

In embodiments where the CPR chest compression machine 400 includes a user interface 414, the user interface may be adapted to output an alert message to a user when the second parameter exceeds the threshold.

Figure 6B:
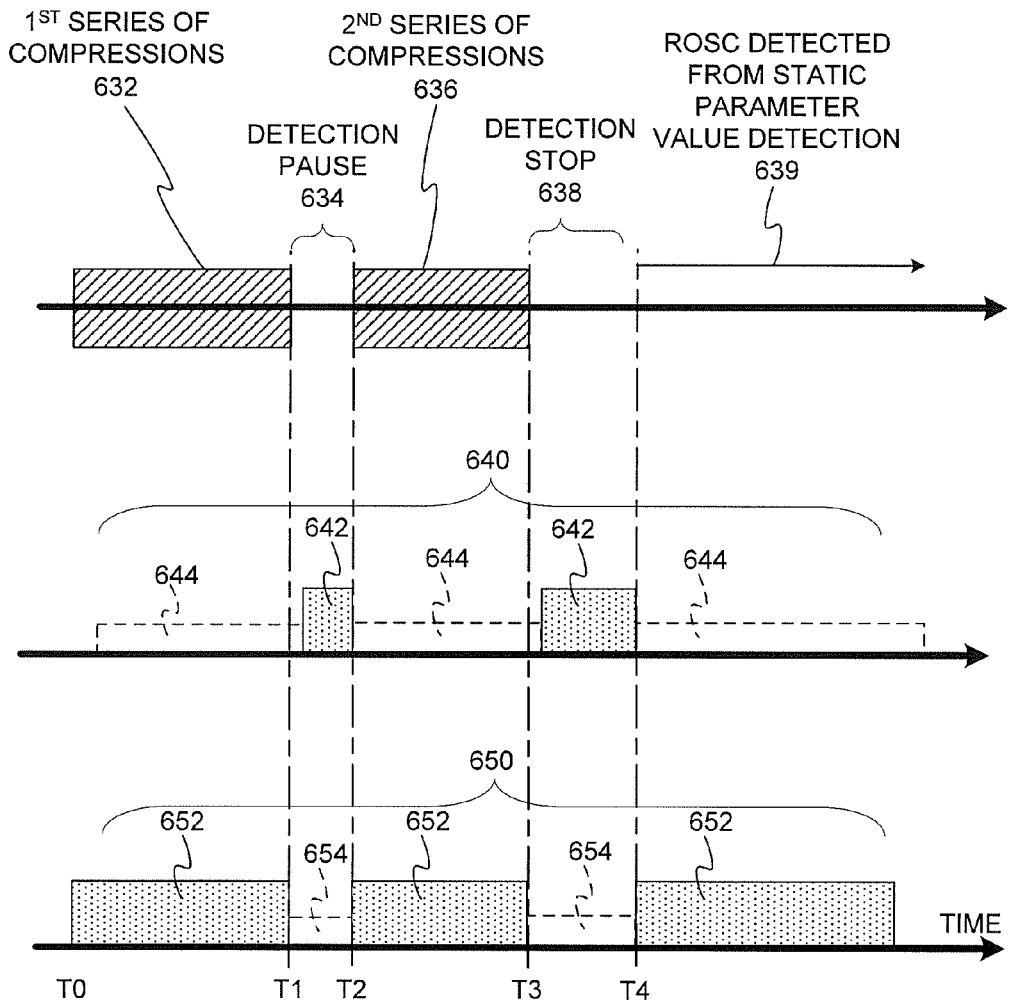
Figure 6C:
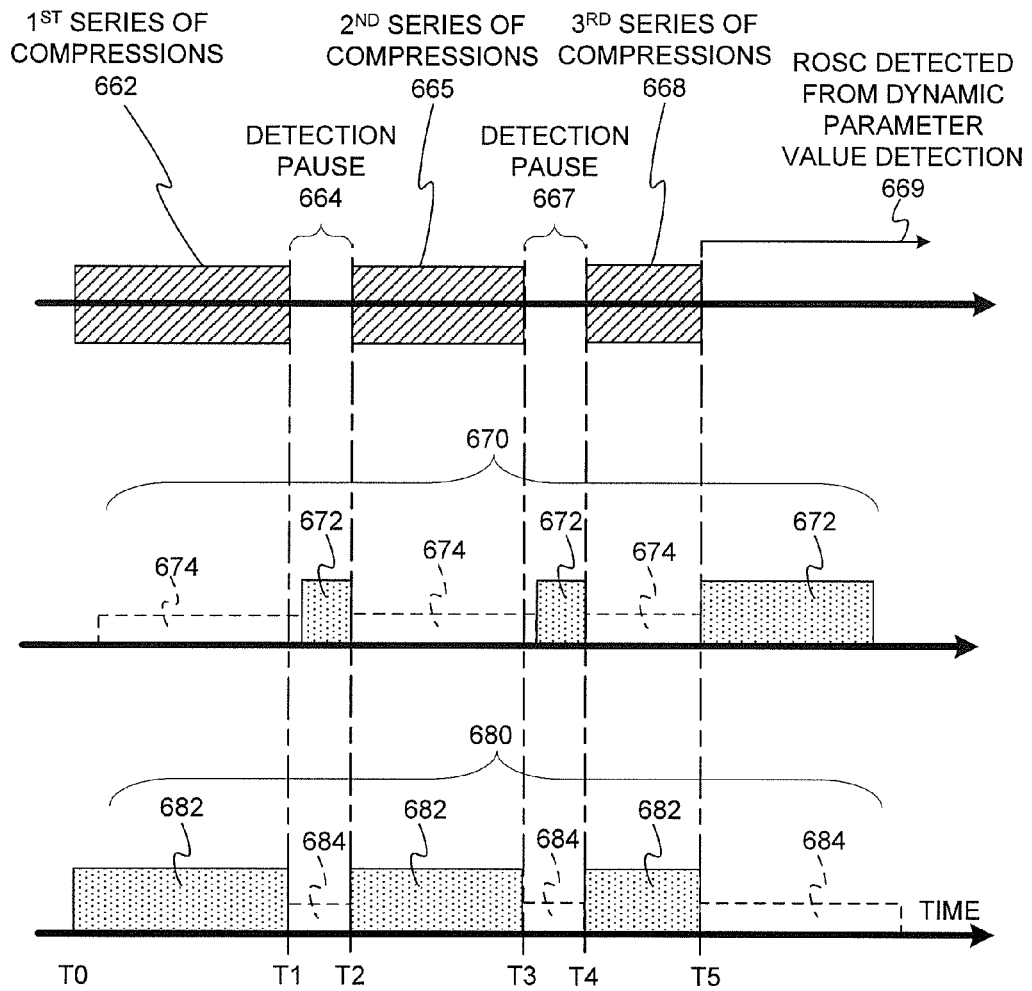

FIGS. 6A, 6B, and 6C are timeline diagrams illustrating dynamic sample detection periods for detecting parameters about a patient during successive chest compressions according to embodiments. In some embodiments, the values of these parameters can ultimately help determine whether Return Of Spontaneous Circulation ("ROSC") has occurred in the patient. While ROSC is mostly described here, there can be other detected conditions that would warrant stopping chest compressions, such as internal trauma, or deteriorating condition, or even futility of CPR such as irreversible-type death.

Referring to FIG. 6A, a first series of compressions 602 are initiated at time T0. In this example, both a first parameter 610 and a second parameter 620 are detected. The first parameter may include detection of a parameter that has more relevant values when the patient is not receiving chest compressions, such as blood velocity, and the second parameter may include detection of a parameter that can be more meaningful by its value changes at the transition time when chest compressions are stopped, such as blood velocity, blood pressure, blood oxygen saturation, end tidal carbon dioxide. Where the decision to restart or prompt from stopping the next series can be based on trending of static and/or dynamic values of parameters. If trending is employed, then suitable thresholds can be set accordingly, such as thresholds of rates, duration, and so on.

Detection of the first parameter 610 and second parameter 620 during this first series of compressions 602 result in respective dynamic values 614, 622. The dynamic values 622 of the second parameter 622 may be more closely monitored during chest compressions for signs of patient recovery. At T1, the processor controls the driver to stop the mechanism from delivering the first series of chest compressions 604 so that static values 612, 624 of the first and second parameter 610, 620 can be detected. Here, the focus of the parameter detection values may shift to the static value 612 related to the detected first parameter. The stopping criteria may be a suitable combination of the static and dynamic values.

In this illustrated example, the static value 612 based on the measured first parameter indicates that the patient is experiencing a Return Of Spontaneous Circulation (ROSC) 606. Hence, a restart condition is not met since the patient may be recovering consciousness, and additional series of successive compressions are not delivered. However, the first and second parameters 610, 620 are still monitored, in case the patient later loses ROSC and required additional chest compressions.

Referring to FIG. 6B, a first series of compressions 632 are initiated at time T0. In this example, both a first parameter 640 and a second parameter 650 are detected. Detection of the first parameter 640 and second parameter 650 during this first series of compressions 632 result in respective dynamic values 644, 652. At T1, the processor controls the driver to stop the mechanism from delivering the first series of chest compressions 634 so that static values 642, 654 of the first and second parameter 640, 650 can be detected.

In this illustrated example, a restart condition is met and a second series of chest compressions 636 is initiated at time T2. Here, during the second series of chest compressions 636, the dynamic value 652 of the detected second parameter 650 indicates that a patient may be recovering and the second series of compressions is stopped at time T3. During this detection stop 638, the first and second parameters 640, 650 are monitored to ensure that the patient has recovered. In this instance, ROSC in the patient is detected from the static value 642 of the first parameter 640 and additional compressions are not delivered to the patient.

Referring to FIG. 6C, a first series of compressions 662 are initiated at time T0. In this example, both a first parameter 670 and a second parameter 680 are detected. Detection of the first parameter 670 and second parameter 680 during this first series of compressions 662 result in respective dynamic values 674, 682. At T1, the processor controls the driver to stop the mechanism from delivering the first series of chest compressions 664 so that static values 672, 684 of the first and second parameter 670, 680 can be detected.

In this illustrated example, a restart condition is met and a second series of chest compressions 665 is initiated at time T2. At T3, the processor again controls the driver to stop the mechanism from delivering the second series of chest compressions 665 so that static values 672, 684 of the first and second parameter 670, 680 can be detected. A restart condition is again met and a third series of chest compressions 668 is initiated at time T4. Here, during the third series of chest compressions 668, the dynamic value 682 of the detected second parameter 680 indicates that a patient is experiencing ROSC 669 and the third series of compressions is stopped at time T5. Although additional series of successive chest compressions are not delivered to the patient, the first and second parameter 670, 680 are continually monitored to ensure that the patient remains in recovery.

The functions of this description may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented by an Application Specific Integrated Circuit (ASIC), etc.

Moreover, methods are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between methods in this description, and the method of operating a computing machine. This description relates both to methods in general, and also to steps for operating a computer and for processing electrical or other physical signals to generate other desired physical signals.

Programs are additionally included in this description, as are methods of operation of the programs. A program is generally defined as a group of steps leading to a desired result, due to their nature and their sequence. A program is usually advantageously implemented as a program for a computing machine, such as a general-purpose computer, a special purpose computer, a microprocessor, etc.

Storage media are additionally included in this description. Such media, individually or in combination with others, have stored thereon instructions of a program made according to the invention. A storage medium according to the invention is a computer-readable medium, such as a memory, and is read by the computing machine mentioned above.

Performing the steps or instructions of a program requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

This detailed description is presented largely in terms of flowcharts, display images, algorithms, and symbolic representations of operations of data bits within at least one computer readable medium, such as a memory. Indeed, such descriptions and representations are the type of convenient labels used by those skilled in programming and/or the data processing arts to effectively convey the substance of their work to others skilled in the art. A person skilled in the art of programming may use these descriptions to readily generate specific instructions for implementing a program according to the present invention.

Often, for the sake of convenience only, it is preferred to implement and describe a program as various interconnected distinct software modules or features, individually and collectively also known as software. This is not necessary, however, and there may be cases where modules are equivalently aggregated into a single program with unclear boundaries. In any event, the software modules or features of this description may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps that may be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

An economy is achieved in the present document in that a single set of flowcharts is used to describe both programs, and also methods. So, while flowcharts are described in terms of boxes, they can mean both method and programs.

For this description, the methods may be implemented by machine operations. In other words, embodiments of programs are made such that they perform methods of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

Methods are now described.

FIG. 7 is a flowchart for illustrating methods for a Cardio-Pulmonary Resuscitation ("CPR") compression machine having a mechanism for delivering successive compressions to a chest of a patient according to embodiments. Although this flowchart illustrates a variety of operations in a particular order, these operations may be carried out in different orders to achieve similar results in other method embodiments. The method shown in this illustrated flow chart may be practiced, for example, by the CPR chest compression machine 400 shown in FIG. 4.

According to an operation 710, a mechanism is controlled to deliver a first series of successive compressions to the chest of the patient. According to another operation 720, the mechanism is then controlled to end delivery of the first series of successive compressions. In another operation 730, a static value of a first parameter about the patient is detected while the patient is not receiving chest compressions. Here, a first sensor signal indicative of the static value is outputted.

According to another operation 740, a constituent value is automatically generated, and from the constituent value it is determined in operation 750 whether a restart condition has been met. If the start condition is met, the mechanism is controlled to deliver a second series of successive compressions in operation 760. If the start condition is not met, successive compressions are not restarted and an optional operation 770 may cause an alert message to be outputted. This alert message may be outputted to a user interface of the machine if the restart condition is not met, or to a device other than the machine if the restart condition is not met.

In operation 740, the automatically generated constituent value may include initiating a timer after the first series of successive compressions has stopped. Here, operation 750 may include determining if the timer has reached a first time interval. Alternatively, operation 750 may include determining if a data measurement corresponding to the first parameter has been completed.

In other embodiments, operation 740 includes rendering a digital value for the static value that has been decoded from the first sensor signal. Here, operation 750 may include determining when the constituent value is first generated, or determining if a computation from the constituent value has been completed Operation 750 may alternately include determining automatically from the first sensor signal that continuing compressions is merited.

The delivery of the first series of compressions in operation 710 may include ventilation pauses for the patient to receive the ventilations, where the first series of compressions is stopped in operation 720 at the beginning of one of the ventilation pauses.

FIG. 8 is another flowchart for illustrating methods for a Cardio-Pulmonary Resuscitation ("CPR") compression machine having a mechanism for delivering successive compressions to a chest of a patient according to embodiments. Although this flowchart illustrates a variety of operations in a particular order, these operations may be carried out in different orders to achieve similar results in other method embodiments. The method shown in this illustrated flow chart may also be practiced, for example, by the CPR chest compression machine 400 shown in FIG. 4.

According to an operation 805, a dynamic value of a second parameter about the patient is detected. According to operation 810, a mechanism is controlled to deliver a next series of successive chest compressions to a patient. The dynamic value of the second parameter in operation 805 is detected while the patient is receiving chest compressions in operation 810. Here, the dynamic value may be received automatically from a second sensor, or may be received via an interface by a human rescuer.

According to another operation 815, it is determined whether the dynamic value of the second parameter indicates that the series of chest compressions should be stopped at a first time. If it is indicated that the compressions should be stopped in operation 815, the mechanism is controlled to end delivery of the series of successive compressions in operation 817. Operation 815 may include determining if the dynamic value exceeds a threshold. As mentioned above, various different parameters and thresholds may be used to determine if the compressions should be stopped. For example, the second parameter may include many different types of data, such as one or more of the following example parameters: 1) Arterial systolic blood pressure, where the threshold may be, for example, about 80 millimeters of mercury; 2) Blood oxygen saturation, where the threshold may be, for example, about 90 percent; 3) End tidal carbon dioxide, where the threshold may be, for example, about 30 millimeters of mercury; 4) Blood velocity, where the threshold may be, for example, zero ml/s; and/or 5) A patient's ECG, where the threshold may be an ECG threshold criterion that is met. Examples of ECG threshold criteria are given above.

The method may also include an optional operation 816 where it is determined if another stopping criterion is met. Here, if another stopping criterion is met, the mechanism is controlled to end delivery of the series of successive compressions in operation 817. In some embodiments, the stopping criterion may be based on previously measured static value, or a combination of the static and dynamic values.

After the compressions are stopped in operation 817, it is determined whether a static value of a patient parameter is to be detected in operation 825. If it is determined that a static value does not need to be detected (e.g., patient recovery is indicated from the detected dynamic parameter in operation 815), an alert message may be outputted in operation 870 to notify a rescuer that the patient may have regained ROSC or that a threshold for the dynamic parameter has been exceeded. In some embodiments, operation 870 may follow directly operation 817.

If it is determined in operation 825 that a static value of a patient parameter is to be measured, the static parameter about the patient is measured in operation 830, and a signal indicating the static parameter value is outputted. Operation 830 may also be reached if the mechanism is controlled to end the series of successive compressions in optional operation 820 without a stopping indication due to the dynamic parameter or another stopping criterion. The successive compressions may be ended at a second time in operation 830 that is determined from a previously measured static value.

If the static value of the patient parameter is measured, a constituent value is generated in operation 840. In operation 850, it is then determined if a restart condition has been met based on the constituent value. The operation 850 may include determining if the static value exceeds a threshold. As discussed above, this operation may include one or more of the following: 1) Determining if an arterial systolic blood pressure of the patient is above about 80 millimeters of mercury; 2) Determining if a blood oxygen saturation of the patient is above about 90 percent; 3) Determining if an end tidal carbon dioxide of the patient is above about 30 millimeters of mercury; 4) Determining if a blood velocity of the patient is above zero ml/s; and/or 5) Determining if a patient's ECG includes an aspect of measured QRS complexes.

If a restart condition is not met in operation 850, an alert message may be outputted in operation 870. Additionally, if the static parameter exceeds a threshold, an alert message may be outputted in operation 870. If a restart condition is met in operation 850, another series of successive compressions may be initiated in operation 810, and some or all of the operations described above may be repeated.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and subcombinations of elements, features, steps, and/or functions, which are regarded as novel and non-obvious. Additional claims for other combinations and subcombinations may be presented in this or a related document.

What is claimed is:

1. A machine for performing Cardio-Pulmonary Resuscitation ("CPR") chest compressions on a patient, the machine comprising:
   a compression structure configured to deliver successive compressions to a chest of the patient;
   a driver configured to drive the compression structure;
   a first sensor adapted to detect a first parameter about the patient and output a first sensor signal indicative of a dynamic value of the first parameter;
   and
   a processor configured to perform operations including:
      controlling the driver to drive the compression structure to deliver a first series of successive compressions,
      determining from the dynamic value whether a stoppage criteria is met,
      after the stoppage criteria is met, controlling the driver to drive the compression structure to stop delivering the first series of successive compressions to detect a static value of the first parameter by the first sensor while the patient is not receiving chest compressions,
      determining from a constituent value whether a restart condition is met, and
      controlling the driver to drive the compression structure to start delivering a second series of successive compressions only when the restart condition is met.

2. The machine of claim 1, in which
the restart condition is met also when a data measurement corresponding to the static value has been completed.

3. The machine of claim 1, in which
the processor is coupled to receive the first sensor signal,
the constituent value is a digital rendering of the static value that has been decoded from the first sensor signal, and
the restart condition is determined when the constituent value is first generated.

4. The machine of claim 1, in which
the processor is coupled to receive the first sensor signal,
the constituent value is a digital rendering of the static value that has been decoded from the first sensor signal, and
the restart condition is determined when a computation from the constituent value is indicated as having been completed.

5. The machine of claim 1, in which
the restart condition is met when a determination has been made automatically from the static value that continuing compressions is merited.

6. The machine of claim 1, in which
the restart condition is determined from a comparison of the static value and the dynamic value.

7. The machine of claim 1, in which
the first series of compressions includes ventilation pauses for the patient to receive the ventilations, and
the first series of compressions is stopped at the beginning of one of the ventilation pauses.
8. The machine of claim 1, further comprising:
a user interface adapted to output an alert message to a user when the restart condition is not met.
9. The machine of claim 1, in which
the processor causes an alert message to be communicated to a device other than the machine when the restart condition is not met.
10. The machine of claim 1, in which
the processor is further adapted to:
   determine whether a stopping criterion is met,
   then control the driver to drive the compression structure to stop delivering the second series of successive compressions when the stopping criterion is met for the first parameter to be detected again by the first sensor while the patient is not receiving chest compressions, and
   then control the driver to drive the compression structure to start delivering a third series of successive compressions.
11. The machine of claim 10, in which
the stopping criterion is determined from the static value.
12. The machine of claim 10, in which
the second series is stopped at a second time determined from the static value.
13. The machine of claim 10, in which
the stopping criterion is met when the detected static value exceeds a threshold.
14. The machine of claim 13, in which
the first parameter includes arterial systolic blood pressure, and
the threshold is about 80 millimeters of mercury.
15. The machine of claim 13, in which
the first parameter includes blood oxygen saturation, and
the threshold is about 90 percent.
16. The machine of claim 13, in which
the first parameter includes end tidal carbon dioxide, and
the threshold about 30 millimeters of mercury.
17. The machine of claim 13, in which
the first parameter includes to blood velocity, and
the threshold is zero ml/s.
18. The machine of claim 13, in which
the first parameter includes a patient's ECG, and
the threshold is an aspect of measured QRS complexes.
19. The machine of claim 13, further comprising:
a user interface adapted to output an alert message to a user when the first parameter exceeds the threshold.
20. The machine of claim 1, further comprising:
a second sensor adapted to detect a dynamic value of a second parameter different from the first parameter, the dynamic value detected about the patient while the patient is receiving the first series of chest compressions, and
the first series of chest compressions is stopped at a first time determined from the dynamic value.
21. The machine of claim 20, in which
the dynamic value is received automatically from the second sensor.
22. The machine of claim 20, in which
the dynamic value is entered via an interface by a human rescuer.
23. The machine of claim 20, in which
the machine stops the second series when the dynamic value exceeds a threshold.
24. The machine of claim 23, in which
the second parameter includes arterial systolic blood pressure, and
the threshold is about 80 millimeters of mercury.
25. The machine of claim 23, in which
the second parameter includes blood oxygen saturation, and
the threshold is about 90 percent.
26. The machine of claim 23, in which
the second parameter includes end tidal carbon dioxide, and
the threshold about 30 millimeters of mercury.
27. The machine of claim 23, in which
the second parameter includes to blood velocity, and
the threshold is zero ml/s.
28. The machine of claim 23, in which
the second parameter includes a patient's ECG, and
the threshold is an included aspect of measured QRS complexes.
29. The machine of claim 23, further comprising:
a user interface adapted to output an alert message to a user when the dynamic value exceeds the threshold.
30. The machine of claim 1, further comprising generation means for automatically generating the constituent value.
31. The machine of claim 1, the processor further configured to control the driver to drive the compression structure to deliver the second series of successive compressions for a length of time based on the first parameter.
32. A method for a Cardio-Pulmonary Resuscitation ("CPR") compression machine having a mechanism configured to deliver successive compressions to a chest of a patient, the method comprising:
   controlling the mechanism to deliver a first series of successive compressions to the chest of the patient;
   detecting a first parameter about the patient and outputting a first sensor signal indicative of a dynamic value of a first parameter,
   determining from the dynamic value whether stoppage criteria is met,
   after the stoppage criteria is met, controlling the mechanism to end delivery of the first series of successive compressions and detecting a static value of the first parameter about the patient while the patient is not receiving chest compressions, and outputting a second sensor signal indicative of the static value of the first parameter;
   automatically generating a constituent value;
   determining from the constituent value whether a restart condition has been met; and
   controlling the mechanism to deliver a second series of successive compressions only when the restart condition is met.
33. An article comprising a storage medium having instructions stored thereon that when executed by at least one device result in:
   controlling a mechanism to deliver a first series of successive compressions to a chest of a patient;
   detecting a first parameter about the patient and outputting a first sensor signal indicative of a dynamic value of the first parameter;
   determining from the dynamic value whether stoppage criteria is met;
   after the stoppage criteria is met, controlling the mechanism to end delivery of the first series of successive compressions and detecting a static value of a first parameter about the patient while the patient is not receiving chest compressions, and outputting a second sensor signal indicative of the static value of the first parameter;

automatically generating a constituent value;

determining from the constituent value whether a restart condition has been met; and controlling the mechanism to deliver a second series of successive compressions only when the restart condition is met.

* * * * *